United States Patent [19]

Schaefer et al.

[11] Patent Number: 5,292,512
[45] Date of Patent: Mar. 8, 1994

[54] COSMETIC OR PHARMACEUTICAL COMPOSITION CONTAINING MICROSPHERES OF POLYMERS OR OF FATTY SUBSTANCES FILLED WITH AT LEAST ONE ACTIVE PRODUCT

[75] Inventors: Hans Schaefer, Antibes; Francine Watts, Le Bar sur Loup; Christos Papantoniou, Montmorency; Claude Mahieu, Paris, all of France

[73] Assignee: Centre Internationale de Recherches Dermatologiques (C.I.R.D.), Valbonne, France

[21] Appl. No.: 451,963

[22] Filed: Dec. 20, 1989

[30] Foreign Application Priority Data

Dec. 20, 1988 [LU] Luxembourg .................. 87 410

[51] Int. Cl.⁵ .................................................. A61K 6/00
[52] U.S. Cl. .................................... 424/401; 424/501; 424/502
[58] Field of Search .................. 424/401, 502, 501

[56] References Cited

U.S. PATENT DOCUMENTS

| | | | |
|---|---|---|---|
| 4,166,800 | 9/1979 | Fong | 424/494 |
| 4,755,387 | 7/1988 | Tzeghai | 424/490 |
| 4,892,733 | 1/1990 | Bichon | 424/422 |
| 4,897,267 | 1/1990 | Bontemps | 424/422 |
| 4,927,883 | 5/1990 | Lapoiriere | 424/489 |
| 4,946,870 | 8/1990 | Partain | 514/945 |
| 4,985,239 | 1/1991 | Yahagi et al. | 424/70 |

*Primary Examiner*—Thurman K. Page
*Assistant Examiner*—Peter F. Kulkosky
*Attorney, Agent, or Firm*—Cushman, Darby & Cushman

[57] ABSTRACT

The invention relates to a pharmaceutical or cosmetic composition for topical application, containing, in a suitable carrier, microspheres of polymers or of fatty substances filled with at least one active product, characterized in that at least 80% of the microspheres employed have a diameter of between 3 μm and 10 μm.

33 Claims, No Drawings

COSMETIC OR PHARMACEUTICAL COMPOSITION CONTAINING MICROSPHERES OF POLYMERS OR OF FATTY SUBSTANCES FILLED WITH AT LEAST ONE ACTIVE PRODUCT

The present invention relates to a cosmetic or pharmaceutical composition containing microspheres of polymers or of fatty substances filled with at least one active product in a suitable carrier.

It is known in the state of the art to prepare microcapsules in which the active principle is enclosed and is not in contact with the external environment (see particularly French Patent 2,218,086 and European Patent 316,054). However, at the time of application, the microcapsule can break prematurely and release the active principle immediately.

It is also known to prepare natural or synthetic polymers in the form of microspheres by crosslinking these polymers in suspension. A process for the manufacture of poly-$\beta$-alanine microspheres is described, for example, in French Patent 2,530,250. It is also known to prepare microspheres of fatty substances.

It is also known that these microspheres are capable of filling with chemical products, in particular with active products (see particularly the abovementioned French Patent and U.S. Pat. No. 4,690,825). In the present application, an active product means any product having an activity from the cosmetic or pharmaceutical viewpoint. The solid product forming the microsphere can, in fact, serve as an absorbent or adsorbent substrate or else as a binder for many chemical products (see European Patent 211,298). The microspheres filled with active products are employed in a suitable carrier in which the solid substrate forming the microspheres is very poorly or not at all soluble. This carrier can be an aqueous solution or an oily phase.

A cosmetic or pharmaceutical composition containing such microspheres filled with active product(s) in a suitable carrier can be employed for bringing medications to a determined point of the body, in particular for application to the skin. However, topical application does not generally have the desired effectiveness because the epidermis forms a barrier.

According to the present invention, it has been found that, if the microspheres of the cosmetic or pharmaceutical composition are chosen from a particular size range, the effectiveness of the active product which they contain is greatly increased in a very unexpected manner. Studies conducted have made it possible to establish that this considerable improvement was linked with the entry of the microspheres into sebaceous follicles.

The subject of the present invention is therefore a cosmetic or pharmaceutical composition for topical application containing, in a suitable carrier, microspheres of natural or synthetic polymers or of fatty substances with a melting point higher than 50° C., filled with at least one active product, characterized in that at least 80% by weight of the microspheres employed have a diameter of between 3 $\mu$m and 10 $\mu$m.

In fact, microspheres which have a diameter in the range defined above enter the sebaceous follicle, but little into the skin. The said microspheres, therefore, selectively and progressively reach the follicular canal, where the active product which they carry diffuses into the follicular canal and the surrounding tissues. On the other hand, the substrate forming the microsphere is subsequently rejected by virtue of the flow of sebum and/or of the growth of hair. Any undesirable reaction of the organism towards the solid compound forming the microspheres is thus avoided.

It should be noted that, when the microspheres have a diameter smaller than 3 $\mu$m, they also enter the follicular canals, but the horny layer as well, in a high concentration. Now, this release of the active principle in the horny layer, for example in the case of antiacne preparations, is reflected by the appearance of secondary effects which are undesirable insofar as the active product is released in the regions of healthy skin which are touched by the application and which surround the follicular channels; whereas, in the case of medications acting systemically, the active product is released in a nonvascularized region where, moreover, the horny barrier intervenes. Overall, therefore, in both cases, the release of the active principle in the horny layer corresponds to a reduction in the effectiveness of the composition. When the microspheres have a diameter greater than approximately 10 $\mu$m, they remain mostly localized on the surface of the skin without entering it, resulting in an ineffectiveness of the topical application, since the active product can only be released on the horny layer. In both cases, the targeting of the active products is markedly inferior to that which is obtained by making use of the invention.

In other words, the invention proposes to select the size of the microspheres so as to promote their selective entry into the sebaceous follicles; in the case of acne, the active product is thus brought specifically to the target regions without undesirable secondary effects on the healthy skin regions surrounding the follicular channels; in the case where the active product is a medication which acts systemically, the follicular channel constitutes a highly efficient route of general administration insofar as the diffusion of the active product into this compartment emerges onto a highly vascularized region.

It was not obvious that microspheres capable of entering the hair follicle had to have the dimensions defined above. In fact, the mean diameter of the pilosebaceous orifices is included in a size range which is quite different from that indicated above in the case of the microspheres; for example, on the forehead, this average diameter is between 52 $\mu$m and 82 $\mu$m. In man, the surface area of the pilosebaceous orifices situated on the forehead is approximately 0.002 mm$^2$ (W. J. Cunliffe, W. D. M. Perera, P. Thackray, M. Williams, R. A. Forster and S. M. Williams, British Journal of Dermatology, 1976, 95, 153). Assuming that the contour of the follicular channel is approximately circular, the average diameter of the pilosebaceous orifices can be estimated, according to this paper, at 50.5 $\mu$m. This diameter, redetermined by measurement of the size of the pilosebaceous orifices situated on the skin of the forehead of six healthy volunteers, is found to be between 52 $\mu$m and 82 $\mu$m (see study described in test B of the present application). This considerable difference between the range of the diameters of pilosebaceous orifices and the range of diameters of the effective microspheres made the invention particularly surprising for the specialist. This surprising nature is furthermore confirmed by the fact that in the abovementioned U.S. Pat. No. 4,690,825, the size indications supplied are aimed only at microspheres which have diameters of between 10 and 100 $\mu$m.

The microspheres which have the desired size can be selected by screening, especially in a moist medium, microspheres obtained by a process giving microspheres which have a more extended range of sizes. It is also possible to obtain microspheres whose sizes are contained in the desired range by suitably directing the process for the manufacture of the microspheres. The size of the microspheres can, for example, be adjusted by choosing the polymerization solvent and the crosslinking agent, or by modifying the rate and the time of stirring of the reaction medium. These various modifications form part of the state of the art and/or are within the competence of the specialist.

The natural or synthetic polymers which can be employed for the manufacture of the microspheres of the composition of the present invention are chosen from those capable of being applied to the skin without undesirable effect and capable of forming microspheres which have the desired dimensions. They must also be compatible with the active product employed.

The polymers which can be employed in the compositions of the present invention may be advantageously chosen from:
- styrene-based polymers, such as polystyrene;
- β-alanine-based polymers, such as poly-β-alanine;
- polymers derived from acrylic or methacrylic acid;
- polyesters derived from lactic and/or glycolic acid;
- proteins crosslinked:
  either by glutaraldehyde or by an acid dichloride such as terephthaloyl chloride,
  or in the presence of an activator such as a carbodiimide;
- proteins coagulated by heat (albumin).

The polymers which can be employed are preferably chosen from polymers based on poly-β-alanine and polyesters derived from lactic or glycolic acid.

The fatty substances which can be employed may be chosen from:
- derivatives of alcohols and of fatty acids, such as tristearin, semisynthetic triglycerides or glycerol monostearate;
- fatty alcohols such as cetyl alcohol.

The fatty substances which can be employed are preferably chosen from fatty substances which have a melting point of approximately between 50° C. and 100° C.

The active products which can be employed in the composition according to the invention are those liable to be applied to the skin. They may be chosen from:
- agents for treating acne, such as compounds with action of retinoid type (vitamin A, retinoic acid or its derivatives);
- benzoyl peroxide;
- growth factors of peptidic nature, such as the proteinic or epidermic growth factor (EGF);
- skin-reinforcing agents, such as benzyl nicotinate;
- agents for treating hair, in particular antiloss or hair regrowth agents, such as minoxidil and antiseborrhoeics such as S-carboxymethylcysteine or octopirox;
- antifungals such as nystatin or econazole;
- astringents, such as aluminium chloride;
- antibiotics, such as erythromycin and tetracycline;
- antivirals, such as vidarabine;
- antihypertensors, such as clonidine hydrochloride;
- antianginals, such as nitroglycerine;
- vasodilators, such as bradikynin;
- agents for treating cardiovascular disorders, such as peptides of the tachykinins group, for example "substance P";
- antiinflammatory agents, such as aspirin or hydrocortisone and its derivatives;
- antiallergens such as chromoglycates;
- antipruritics, such as phenothiazine derivatives;
- neurostimulants, such as caffeine or theophylline;
- antidepressant agents, such as lithium salts and, more particularly, lithium carbonate;
- natural compounds employed in neurobiological research, such as capsaicine;
- anaesthetics, such as lidocaine and procaine;
- hormone steroids such as 17-α-oestradiol and 17-β-oestradiol.

The suitable carrier is in aqueous form or in the form of oil.

The carrier in aqueous form may be an aqueous gel obtained with the aid of a gelling agent, such as the crosslinked polyacrylic acid sold under the trade name "Carbopol" by Goodrich BF or the cellulose derivatives sold under the trade name "Klucel" by Hercules; or a hydroalcoholic gel containing, for example, propylene glycol. It is also possible to use a lipophilic aqueous solution such as an aqueous solution of silicones.

The oils which can be employed as carriers are liquid or semisolid oils such as triglycerides of $C_8$–$C_{10}$ fatty acids and their mixtures, vaseline, liquid paraffin and lanolin.

The Ph of the carrier is preferably adjusted to a basic value.

The carrier is in the form of liquid, of gel, of cream, of paste, of pomade or of dry powder. To obtain a paste, a pomade or an ointment, an excipient is added, such as polyethylene glycol, a wax such as beeswax or lanolin.

The cosmetic or pharmaceutical compositions according to the present invention generally contain from 1% to 40% by weight of microspheres, at least 80% of which have diameters of between 3 and 10 μm.

They also contain from 0.05% to 60% by weight of active product.

The microspheres are manufactured by any known process. The polystyrene microspheres are widely marketed. Those of poly-β-alanine can, for example, be prepared according to the processes described in French Patent 2,530,250.

To introduce the active product into the microsphere, the active product is dissolved in a solvent or a mixture of solvents which have a sufficient affinity for the compound forming the microspheres. Among the suitable solvents, especially for poly-β-alanine spheres, there may be mentioned, for example, water, glycerol, ethanol, diethylene glycol, acetone and, in general, water-miscible organic solvents.

When a solvent has been employed to obtain the microspheres filled with active product, the said microspheres may be employed as such or after removal of the solvent remaining therein. This solvent may have remained therein as solvent of the active product and/or as a swelling agent for the microsphere itself when the polymer of which it is made is liable to swell in the said solvent. When the microspheres are employed after removal of the solvent, the active product remains nevertheless trapped in (or on) the microsphere on drying. Swelling of the polymer by a solvent produces microspheres in gel form, provided that the quantity of solvent does not exceed certain limits, which are different depending on the polymer of which the microspheres are made. The microspheres filled with at least one active product, be they dried or not, are mixed with the chosen carrier.

The cosmetic or pharmaceutical composition obtained is applied in the usual way to the skin, preferably with a gentle massage. In an alternative form, the microspheres are filled with an active product in ionized form: in this case, after application of the composition to the skin, the release of the active product may be accelerated by ionophoresis.

The examples given below, purely by way of illustration, no limitation being implied, will allow the invention to be better understood. Tests A, B and C are measurements provided to explain the remarkable effectiveness of the compounds according to the invention.

Test A

In this test, the size of the pilosebaceous orifices in man is evaluated. This study was carried out on six healthy volunteers (three men and three women) aged from 25 to 35 years, and it was carried out on the skin of the forehead.

After having carefully cleaned with soap a region of skin of approximately 2 cm², a dye (dark brown direct dye "L'Oreal renovative", marketed by the company known as "l'Oreal") is chosen and is applied, for fifteen minutes, to the left or right side part of each subject's forehead. At the end of the exposure time, the colored region is cleaned with a little water to remove the excess dye. This region is photographed with a macrophotographic assembly produced with the aid of an Olympus camera. This apparatus makes it possible to take standardized photographs of the region to be analysed (same distance and some magnification for all the subjects). The dye employed is no longer visible 24 hours after the application.

The distribution of sizes of the pilosebaceous orifices is established by image analysis with the aid of the "Quantimet 520" apparatus from Cambridge Instruments, from transparencies of the forehead. The apparatus measures the surface area S of the follicle openings and calculates the diameter D of each follicle according to the formula:

$$D = 2(S/x)$$

The results are given in Table 1 below.

The average diameter of the follicles is found to be between 52 μm and 82 μm for all the subjects studied.

Test B

Tests were carried out to establish the relationship between the size of the microspheres and their entry through the horny layer and the follicles of the human skin.

These tests employed fluorescent polystyrene microspheres of various calibers between 1 μm and 24 μm which had the characteristics given in Table II below. These batches of polystyrene microspheres were suspended at a concentration of 10% by weight in a mixture of triglycerides of $C_8$-$C_{10}$ fatty acids marketed under the trade mark "Mygliol 812" by Dynamit Nobel; the tests were performed on the face lift skin of the face of female patients aged from 44 to 66 years.

TABLE I

| SUBJECT NO. | SEX | SURFACE FOLLICLES | DIAMETER (μm) Average +/− standard deviation | <90% | <95% |
|---|---|---|---|---|---|
| 1 | M | 105 | 82 +/− 34 | <128 | <150 |
| 2 | F | 102 | 68 +/− 42 | <120 | <141 |
| 3 | F | 111 | 82 +/− 43 | <133 | <158 |
| 4 | F | 116 | 52 +/− 25 | <87 | <99 |
| 5 | M | 108 | 79 +/− 37 | <128 | <143 |
| 6 | M | 68 | 79 +/− 31 | <124 | <132 |

TABLE II

| Average diameter* (μm) | | Standard deviation* (μm) | Polysciences Inc. microspheres reference | Fluorescence type** |
|---|---|---|---|---|
| Precise value | Rounded-off value | | | |
| 0.91 | 1 | 0.06 | 17154 | yellow-green |
| 1.17 | 1 | 0.04 | 17458 | bright blue |
| 3.1 | 3 | 0.1 | 17155 | yellow-green |
| 6.83 | 7 | 0.2 | 18141 | yellow-green |
| 7.0 | 7 | 0.3 | 17156 | yellow-green |
| 9.13 | 9 | 0.6 | 18140 | yellow-green |
| 9.55 | 10 | 1.53 | 18142 | yellow-green |
| 23.8 | 24 | 4.2 | 18241 | yellow-green |

*The size analyses of these particle size standards were supplied by OSI (Polysciences Inc.).
**Fluorescence type: (see Table III).

TABLE III

| Fluorescence | Excitation max. (nm) | Emission max. (nm) |
|---|---|---|
| Bright blue | 365 | 468 |
| Yellow-green | 458 | 540 |

The applications are carried out, approximately 4 hours after surgical excision, on facial skin which has not been deep-frozen (storage at 4° C. in a cold chamber). The skin is freed from its subcutaneous tissue with a scalpel, and is then slightly stretched and pinned onto a support covered with aluminum. The cutaneous surface is carefully cleaned by wiping with a paper handkerchief, followed by a slight "stripping" carried out with the adhesive tape sold under the trade name "Transpore". The various suspensions of microbeads are then applied with a glass spatula for 15 minutes, with 5 minutes' massage, inside 2.5-cm² application sites delimited by plastic rings bonded using a cyanoacrylate polymer-based adhesive marketed under the name of "Cyanolit". At the end of the application time, the excess product which has not entered the skin is removed with a cotton-stick followed by three very slight applications, to the surface of the skin, of a piece of adhesive tape of trade name "Transpore" (adhering little to the skin and causing no delamination of the horny layer). Biopsies of the application sites, as well as of a control skin region without application, are taken with a "Punch biopsy" punch 6 mm in diameter and are frozen in liquid nitrogen. The entry of the microbeads into the horny layer and the follicles is then demonstrated, using a fluorescence optical microscope (photomicroscope IIIRS, Zeiss, West Germany) on deep-frozen vertical skin sections 10 μm to 15 μm in thickness, produced with the aid of a cryomicrotome (Cryostat Bright, Bright Instrument Company Limited).

The results obtained are the following:
microspheres 24 μm in diameter remain localized on the surface of the skin without entering it;

microspheres 9 μm to 10 μm in diameter have a tendency to collect around the follicular canals;

7-μm microspheres have been able to be selectively placed inside the sebaceous follicles;

microspheres from 1 μm to 3 μm have a tendency to enter both the horny layer and the follicles.

Test C

Tests were carried out to establish the relationship between the size of the microspheres and their entry into the horny layer and the follicles in the rat.

These tests employed poly-β-alanine microspheres; three samples which had average diameters of approximately 2 μm, 5 μm and 12 μm respectively were tested.

The microspheres employed are prepared by crosslinking poly-β-alanine with the aid of glutaraldehyde. This synthesis is described in French Patent 2,530,250. These microspheres are then made fluorescent by an intermediate reaction of hexamethylenediamine with the residual aldehyde functional groups present at their surface, followed by a reaction with dansyl chloride. The microspheres obtained exhibit a very homogeneous powerful green fluorescence in ultraviolet light. These microspheres have the following characteristics:

sample 1: diameter=1.79±0.86 μm (90% below 2.9 μm);

sample 2: diameter=4.8±1.1 μm (90% below 6.1 μm); prepared according to Example 1;

sample 3: diameter=12.4±2.2 μm (90% below 15.1 μm).

These size measurements were determined by the fluoresence image analysis technique 520" apparatus marketed by Cambridge Instruments Co.

The application protocol employed is the following: after anaesthesia with pentobarbital (30 mg/kg dose), 5-cm² application sites are delimited by a plastic ring bonded adhesively to the back of the ICO female nude rat (170–180 g average weight). The various suspensions are applied for 2 hours, in a quantity of 5 to 10 mg/cm², inside these sites. In order to test the influence of massage on the entry of the poly-β-alanine microspheres into the sebaceous follicles, the application is carried out by comparing two massage periods: one minute and five minutes. The animal is bound throughout the experimental period in order to avoid any contact with the region of application. At the end of 2 hours, the excess product which has not entered the skin is carefully removed with a cotton-stick; three very slight applications of a piece of adhesive tape of trade name "Transpore" (adhering little to the skin and causing no delamination of the horny layer) to the skin surface are then carried out. Biopsies of the application regions are taken (6 mm in diameter) and frozen in liquid nitrogen. The entry of the microspheres into the horny and follicular compartments is then established using the fluorescence optical microscope on deep-frozen vertical skin sections from 10 μm to 15 μm in thickness, produced using the cryomicrotome.

In order to test the influence of the carrier on the entry of the poly-β-alanine microspheres, the latter are formulated, at a concentration of 10% by weight, in the following carriers:

| 1) Aqueous gel which has the following formulation: | |
|---|---|
| Crosslinked polyacrylic acid sold under the trade name "Carbopol 940" by Goodrich BF | 0.4 g |
| Sodium hydroxide (aqueous solution at a concentration of 10% by weight) | |
| Water q.s. | 100.0 g |
| 2) Water-silicone carrier consisting of: | |
| Water | 5.0 g |
| Silicone oil sold by Dow Corning under the reference "Q2-3225c" q.s. | 100.0 g |

The results are as follows:

a) in suspension in the aqueous gel, microspheres 2 μm in diameter enter the various layers of the horny layer as well as inside the follicular canals. 5-μm microspheres are rarely present in the horny layer, after one minute's massage, and are located rather at the entry of the follicular canals; this tendency to enter the follicles is slightly more pronounced after 5 minutes' massage. Microspheres 12 μm in diameter enter neither the horny layer nor the follicular canals.

b) the water-silicone carrier has an influence on the entry of the 2-μm microspheres: the latter are more numerous inside the sebaceous follicles and exhibit a uniform distribution in the horny layer. On the other hand, with this carrier, practically no 5-μm microspheres are found in the horny layer: they are located very deep in the follicles in the vicinity of the sebaceous glands; in this case, massage also has a beneficial influence on the entry of the microspheres into the follicular compartment. As in the case of the aqueous gel, microspheres 12 μm in diameter enter neither the horny layer nor the follicles.

Examples 1 to 6 below describe processes for the manufacture of poly-β-alanine microspheres, fluorescent or filled with active products and having the desired diameter.

EXAMPLE 1

PREPARATION OF FLUORESCENT POLY-β-ALANINE MICROSPHERES

STAGE A

Preparation of poly-β-alanine spheres in suspension 1125 g of toluene, 444 g of tert-butanol and 0.75 g of copolymer (octadecene/maleic anhydride) (sold under the trade name "PA-18" by Gulf) are introduced into a 3-liter reactor equipped with an anchor-type stirrer with a diameter of 90 mm, a nitrogen inlet, a dropping funnel and a distillation column head. After heating this mixture to 70° C., 150 g of acrylamide are added. The temperature is then raised to 100° C. and 90 ml of the azeotrope mixture (water/toluene/tert-butanol) are distilled off. After the end of distillation, the reaction mixture is cooled to 80° C. and the stirring rate is adjusted to 600 rev/min. A solution of 3.30 g of potassium tert-butylate in 62 g of tert-butanol is then added over 10 minutes. The dropping funnel is rinsed with 75 g of toluene. After stirring for 5 hours at 80° C., the material is allowed to return to ambient temperature. 11.25 ml of concentrated hydrochloric acid are then added dropwise to the mixture.

Stage B

Crosslinking of the poly-β-alanine spheres 42 g of an aqueous solution containing 25% of glutaraldehyde are added to the suspension of poly-β-alanine microspheres thus obtained, over 30 minutes, with stirring at 600 rev/min and at a temperature of 50° C. After stirring has been continued for 4 hours at this temperature, the suspension is allowed to return to ambient temperature.

After settling, the supernatant solvents are removed and the microspheres are washed twice with 500-ml portions of ethanol. Draining after each washing is carried out by centrifuging at 3,500 rev/min. A washing with 15 liters of water is then carried out continuously and the water is then removed to a final mixture volume of 600 ml is reached.

The crosslinked poly-$\beta$-alanine is then dried by freeze-drying and 135 g of a white powder are obtained, in which the diameter of the microspheres is on average 4.80±1.1 µm, determined by the image analysis technique using a "Quantimet 520" apparatus marketed by Cambridge Instruments Co..

Stage C

Reaction with 1,6-diaminohexane 20 g of 1,6-diaminohexane are added to a suspension of 20 g of the poly-$\beta$-alanine spheres obtained in stage B in 100 g of water. Stirring is continued for 24 hours at ambient temperature and the material is then drained in a no. 4 glass sinter: lastly, it is washed with water until the aqueous washers are at a neutral pH.

Stage D

Fixing of the fluorescent product.

The microspheres obtained in stage C are suspended in 80 ml of pH 8.9 buffer solution (270 ml of 0.1M NaHCO$_3$ solution brought to pH=8.9 by adding approximately 30 ml of 0.1M solution of Na$_2$CO$_3$). 2 g of dansyl chloride in solution in 80 g of acetone are introduced into this suspension. The mixture is heated for 10 minutes at solvent reflux and is then drained on a no. 4 glass sinter and finally washed with acetone until all traces of dansyl chloride have disappeared from the solvent wash, monitored by UV detection at 250 nm. The spheres are first dried in air and then under reduced pressure at ambient temperature. The final color of the microspheres is light yellow.

EXAMPLE 2

Preparation of Poly-$\beta$-Alanine Microspheres Filled with Benzoyl Peroxide

Stage A

Preparation of poly-$\beta$-alanine spheres in suspension
This stage is identical with stage A of Example 1.

Stage B

Crosslinking of the poly-$\beta$-alanine microspheres 18 g of aqueous solution containing 25% by weight of glutaraldehyde are added steadily over 15 minutes to a suspension of poly-$\beta$-alanine microspheres obtained in stage A, kept vigorously stirred (600 rev/min) and at a temperature of 50° C. After stirring has been continued for 4 hours at this temperature, the suspension is allowed to return to ambient temperature. After settling, the supernatant solvents are removed and the microspheres are washed twice with 500-ml portions of ethanol. The draining after each washing is carried out by centrifuging (3,500 rev/min). Washing with 15 liters of water is then carried out continuously and the water is then removed until a final mixture volume of 600 ml is reached. The swollen polymer is finally dried by freeze-drying and 132 g of white powder are obtained, in which the diameter of the microspheres is on average 4.05±2.02 µm, measured according to the same method as in Stage B of Example 1.

Stage C

Reduction of the residual aldehyde functional groups.

2.2 liters of water are added to 150 g of crosslinked poly-$\beta$-alanine microspheres obtained in stage B and are homogenized by stirring. After cooling to a temperature of between 5° and 10° C., a cooled solution of sodium borohydride in water (5.2 g of NaBH$_4$ in 600 ml of water cooled to 5° C.) is added slowly. The reaction mixture is kept between 5° and 10° C. for 5 hours and the pH is then brought to 7 by adding acetic acid.

After centrifuging the mixture and dispersing the solid residue in 450 ml of water, it is subjected to continuous washing with 5 liters of water (washing in an "Amicon" cell equipped with a 0.2-µm Diapor filter, pressure 2 bars, stirring throughout the washing). The hydrated microspheres are then dried by freeze-drying. The absence of color in the presence of Schiff's reagent makes it possible to conclude that the residual aldehyde functional groups have been reduced. After analysis, the diameter of the microspheres is identical with that of the original microspheres.

Stage D

Introduction of the active product 44.5 g of benzoyl peroxide (75% by weight grade) are dissolved in a mixture made up of 1125 g of acetone and of 375 g of water; 50 g of the microspheres prepared in stage C are then suspended in this solution. The suspension is concentrated in a rotary evaporator at reduced pressure, at a temperature not exceeding 35° C., to a total weight of 262 g of suspension.

The benzoyl peroxide content of the suspension obtained is 9.1% by weight.

EXAMPLE 3

Preparation of Poly-$\beta$-Alanine Microspheres Filled with Benzyl Nicotinate

Stages A to C

Preparation of the microspheres
Stages A to C are carried out as in Example 2.

Stage D

Introduction of the active product 2 g of benzyl nicotinate are dissolved in a mixture made up of 40 g of water and 40 g of ethanol; 10 g of microspheres prepared in Stage C are then suspended in this solution. The suspension is kept stirred for 2 hours and the ethanol is then removed in a rotary evaporator, the temperature being maintained at a value below 35° C. Finally, the microspheres are dried by freeze-drying.

EXAMPLE 4

Preparation of Poly-$\beta$-Alanine Microspheres Filled with Benzyl Nicotinate

Stages A to C are carried out as in Example 1 and stage D for introducing benzyl nicotinate as active product, as in Example 3.

EXAMPLE 5

Preparation of Poly-$\beta$-Alanine Microspheres Filled with Retinoic Acid

Stages A to C

Preparation of the microspheres

Stages A to C are carried out as in Example 2.

Stage D

Introduction of the active product 15 mg of butylhydroxytoluene (antioxidant) are dissolved in 30 g of 1,2-propylene glycol at a temperature of 30° C. 24 mg of retinoic acid are dissolved in 10 g of the mixture obtained above, at ambient temperature, under argon and in the absence of light. The solution obtained is filtered with the aid of 0.2-μm "Millipore" filters. 5 g of the microspheres prepared in stage C are suspended in this solution in the absence of light and under a stream of argon. Mixing is carried out with a spatula. After two hours' absorption, a yellow powder is obtained. Determination of retinoic acid in the spectrophotometer ($\lambda$=358.8 nm) after desorption of the active principle into dimethyl sulphoxide.

Theoretical concentration: 0.16%.

Calculated concentration: 0.157%.

EXAMPLE 6

Preparation of Poly-β-Alaline Microspheres Filled with Clonidine Hydrochloride

Stages A to C

Preparation of the microspheres

Stages A and C are carried out as in Example 2.

Stage D

Introduction of the active product 37.6 mg of clonidine hydrochloride are dissolved in 15 g of water in the absence of light, and 3 g of microspheres prepared in stage C are then added to 12 g of the above solution. Mixing is carried out with a spatula. After 2 hours' absorption a white powder is obtained. The microspheres are then dried by freeze-drying. Determination of clonidine hydrochloride in the finished product is carried out by HPLC analysis after desorption of the active principle.

Calculated concentration: 1%.

EXAMPLE 7

Preparation of Poly-β-Alanine Microspheres Filled with Minoxidil

Stages A to C

Preparation of the microspheres

Stages A and C are carried out as in Example 2.

Stage D

Introduction of the active product 2 g of minoxidil are dissolved at 30° C. in a mixture made up of 75 g of ethanol and 75 g of water. 8 g of poly-β-alanine spheres obtained according to stage C are introduced into this solution. The mixture is stirred for 1 hour in the rotary evaporator and the solvent is then evaporated off until a gel is obtained. The gel is frozen with stirring and then freeze-dried.

Calculated concentration: 11.6% (by UV determination at 230 nm after suspending in ethanol).

EXAMPLE 8

Preparation of Fatty Substance Microspheres Filled with Retinoic Acid

Stage A

Preparation of the solution of active principle 200 mg of all-trans retinoic acid are dissolved in 5 ml of 1,2-dichloroethane, in the absence of light.

Stage D

Coating of the active principle with fatty substance microspheres 4.75 g of tristearin and 250 mg of glycerol monostearate are introduced into a stainless steel reactor provided with a nitrogen inlet and equipped with a magnetic stirrer and a heating plate. Mixing is carried out by stirring at a temperature of 80° C. The solution of active principle prepared in stage A is then added in the absence of light. The mixture obtained is kept stirred at 80° C. and is then blown, under a nitrogen pressure of 7 bars, into a spraying nozzle connected to the reactor Apparatus "¼ JCO-SS-SU.B15B-SS", Emani). The microspheres consisting of the retinoic acid coating with the mixture of tristearin-glycerol monostearate fatty substances are then formed downstream of this spraying nozzle inside a filtration chamber (length: 85 cm) and are then collected on a grid (Millipore, 24 cm in diameter, preferably, "1 YY30 293 58"). A yellow-colored powder is obtained. The retinoic acid content of the microspheres obtained is 2.78% by weight. The diameter of the microspheres, determined by image analysis (MOP-Videoplan Apparatus, Kontron) is 4.43±1.08 μm.

Example 9 to 18 below relate to the preparation of cosmetic or pharmaceutical compositions from microspheres filled with active product and prepared in Examples 2 to 8.

EXAMPLE 9

Preparation of Poly(Lactide-Co-Glycolide) Microspheres Filled with 6-[3-(1-Adamantyl-4-Methoxyphenyl)]-2-Naphthoic Acid 0.5 g of poly(lactide-co-glycolide) sold by Dupont under the trade name of "Medisorb 5050 DL" and 5 mg of 6-[3-(1-adamantyl-4-methoxyphenyl)]-2-naphthoic acid are dissolved in 15 ml of methylene chloride. The organic solution obtained is emulsified with mechanical stirring (2000 rev/min) in 100 ml of an aqueous gel containing 0.3 g of hydroxypropyl cellulose sold by Aqualon under the trade name of "Klucel HF". Mechanical stirring is continued for 2 hours, which permits the progressive and complete evaporation of methylene chloride.

The microspheres obtained are recovered, washed three times with distilled water and freeze-dried. The size distribution of the microspheres obtained by this method is analyzed with a microscope. The diameter of the spheres is between 1 and 15 μm, with an average size of 5 μm, more than 80% of the microspheres have a diameter of between 3 and 10 μm.

The encapsulation is checked in the following manner:

1) inspection of the microspheres by optical microscopy (fluorescence) shows fluorescent spheres and the absence of free crystals of active principle, 2) inspection by electron microscopy confirms the absence of crystals outside the spheres and the absence of crystals on the surface of the spheres.

To evaluate the degree of encapsulation of the active principle in the microspheres, a sample of the microspheres obtained above (100 mg) is extracted with tetrahydrofuran (5 ml); it is then filtered; the filtrate is analysed by high performance liquid chromatography: the degree of encapsulation of 6-[3-(1-adamantyl-4-methoxyphenyl)]-2-naphthoic acid is 0.75%.

EXAMPLE 10

PREPARATION OF POLY(LACTIDE-CO-GLYCOLIDE) MICROSPHERES FILLED WITH RETINOIC ACID

Microspheres filled with retinoic acid can be obtained by the same method of preparation as in Example 9: the 5 mg of 6-[3-(1-adamantyl-4-methoxyphenyl)]-2-naphthoic acid are then replaced by 2 mg of retinoic acid.

EXAMPLE 11

PREPARATION OF TRIGLYCERIDE MICROSPHERES FILLED WITH N-BENZYLPHENYLACETOXYACETAMIDE

Microspheres are prepared from triglycerides, namely a hydrogenated palm oil marketed under the name of "Softisan 154" by Dynamit Nobel, by a spraying process with the aid of a pressurized spraying unit.

The triglyceride and the active principle, namely N-benzylphenylacetoxyacetamide at a concentration of 15% by weight relative to the weight of triglycerides, are melted at 90° C. under nitrogen atmosphere and in the absence of light in a thermostated stainless steel reactor. The molten mixture is propelled with nitrogen ($0.5 \times 10^2$ kPa pressure) up to the nozzle at a certain flow rate and the spraying is carried out at the nozzle under nitrogen pressure ($3 \times 10^2$ kPa pressure).

The spraying is carried out in a sealed stainless steel vessel which has a temperature gradient from approximately $-150°$ C. at the bottom to 20° C. at the top. This gradient is created by previous introduction of liquid nitrogen into the bottom of the vessel.

As a general rule, depending on the type of nozzle which is chosen, the spraying nitrogen pressure and the flow rate of the liquid determine the average diameter of the spheres obtained. Thus, the lower the flow rate, the smaller the droplets leaving the nozzle and, consequently, the microspheres at the bottom of the vessel. Furthermore, the higher the spraying pressure, the smaller the diameter of the spheres and the more homogeneous the size distribution.

In this example, uniform microspheres are obtained without free crystals of active principle which are visible under the microscope. The diameter of the spheres varies from 1 to 15 μm, with a mean diameter below 10 μm. The proportion of active principle incorporated, determined by high performance liquid phase chromatography, was established at 15%.

EXAMPLE 12

A gel is prepared by mixing the following ingredients:

| | |
|---|---|
| Microsphere suspension prepared according to Example 2 | 262 g |
| Water q.s. | 900 g |
| Crosslinked polyacrylic acid sold under the trade name "Carbopol 940" by Goodrich BF | 3.6 g |
| Sodium hydroxide q.s. | pH = 7 |

When applied to the skin by massage until it enters completely, twice daily for 30 days, this preparation has excellent antiacne properties.

EXAMPLE 13

A gel is prepared by mixing the following ingredients:

| | |
|---|---|
| Microsphere suspension prepared according to . Example 2 | 262 g |
| Water q.s. | 445 g |

When applied to the skin by massage until it enters completely, twice daily for 30 days, this preparation has excellent antiacne properties.

EXAMPLE 14

A gel is prepared by mixing the following ingredients:

| | |
|---|---|
| Microsphere suspension prepared according to Example 2 | 262 g |
| Crosslinked polyacrylic acid sold under the trade name "Carbopol 940" by Goodrich BF | 22 g |
| Water q.s. | 4.4 kg |
| Sodium hydroxide q.s. | pH = 7 |

When applied to the skin by massage until it enters completely, twice daily for 30 days, this preparation has excellent antiacne properties.

EXAMPLE 15

A gel is prepared by mixing the following ingredients:

| | |
|---|---|
| Microspheres prepared according to Example 3 (as many as are necessary) | 1 g |
| Crosslinked polyacrylic acid sold under the trade name "Carbopol 940" by Goodrich BF | 0.4 g |
| Water q.s. | 100 g |
| Sodium hydroxide q.s. | pH = 7 |

When applied by massage until it enters completely, twice daily for 30 days, to certain parts of the body, for example the breasts, this preparation contributes to making them firmer.

EXAMPLE 16

A gel is prepared by mixing the following ingredients:

| | |
|---|---|
| Microspheres prepared according to Example 4 (as many as are necessary) | 1.2 g |
| Crosslinked polyacrylic acid sold under the trade name "Carbopol 940" by Goodrich BF | 0.4 g |
| Water q.s. | 100 g |
| Sodium hydroxide q.s. | pH = 7 |

When applied by massage until it enters completely, twice daily for 30 days, to certain parts of the body, for example the neck, this preparation contributes to making them firmer.

EXAMPLE 17

A gel is produced by mixing the following ingredients:

| | |
|---|---|
| Microspheres obtained in Example 5 | 33 g |
| Silicone oil sold by Prolabo under the reference | 100 g |

-continued

| | |
|---|---|
| "Rhodorsil RTV 70141" q.s. | |

When applied to the skin by massage until it enters completely, twice daily for 30 days, this preparation has excellent antiacne properties.

EXAMPLE 18

A gel is prepared by mixing the following ingredients:

| | |
|---|---|
| Microspheres obtained in Example 5 | 33 g |
| Silicone oil sold by Dow Corning under the reference "DC 344" q.s. | 100 g |

When applied to the skin by massage until it enters completely, twice daily for 30 days, this preparation has excellent antiacne properties.

EXAMPLE 19

A gel is prepared by mixing the following ingredients:

| | |
|---|---|
| Microspheres obtained in Example 6 | 30 g |
| Cellulose derivatives sold under the trade name "Klucel" by Hercules | 1.5 g |
| Water q.s. | 100 g |

When applied to the skin by massage until it enters completely, twice daily for 2 to 3 weeks, this preparation has excellent antihypertensive properties.

EXAMPLE 20

A gel is prepared by mixing the following ingredients:

| | |
|---|---|
| Microspheres obtained in Example 7 | 17.24 g |
| Cellulose derivatives sold under the trade name "Klucel" by Hercules | 1.66 g |
| Water | 16.22 g |
| Propylene glycol q.s. | 100 g |

This gel is applied twice daily to a scalp which has undergone a considerable hair loss. After 3 months' treatment at a rate of 1 ml per application a significant improvement is noted.

EXAMPLE 21

A gel is prepared by mixing the following ingredients:

| | |
|---|---|
| Microspheres obtained in Example 8 | 1.8 g |
| Cellulose derivatives sold under the trade name "Klucel" by Hercules | 1.47 g |
| Water q.s. | 100 g |

When applied to the skin by massage until it enters completely, twice daily for 30 days, this preparation has excellent antiacne properties.

EXAMPLE 22

A gel is prepared by mixing the following ingredients:

| | |
|---|---|
| Microspheres prepared according to Example 9 | 15 g |
| Crosslinked polyacrylic acid sold under the name "Carbopol 940" by Goodrich BF | 0.4 g |
| Water q.s. | 100 g |
| Sodium hydroxide q.s. | pH = 7 |

When applied to the skin by massage until it enters completely, twice daily for 30 days, this preparation has excellent antiacne properties.

EXAMPLE 23

A gel is prepared by mixing the following ingredients:

| | |
|---|---|
| Microspheres prepared according to Example 10 | 5 g |
| Crosslinked polyacrylic acid sold under the name "Carbopol 940" by Goodrich BF | 0.4 g |
| Water q.s. | 100 g |
| Sodium hydroxide q.s. | pH = 7 |

When applied to the skin by massage until it enters completely, twice daily for 30 days, this preparation has excellent antiacne properties.

EXAMPLE 24

A gel is prepared by mixing the following ingredients:

| | |
|---|---|
| Microspheres prepared according to Example 11 | 20 g |
| Crosslinked polyacrylic acid sold under the name "Carbopol 940" by Goodrich GF | 0.4 g |
| Water q.s. | 100 g |
| Sodium hydroxide q.s. | pH = 7 |

When applied to the skin by massage until it enters completely, twice daily for 30 days, this preparation has excellent antiinflammatory properties.

What is claimed is:

1. A pharmaceutical or cosmetic composition for topical application to the skin comprises, in a pharmaceutically or cosmetically acceptable carrier for topical application to the skin, microspheres of a polymer or fatty substance having a melting point approximately higher than 50° C., said microspheres being filled with at least one pharmaceutically or cosmetically active product and having a size such that they enter the sebaceous follicle on topical application to the skin and selectively and progressively reach the follicular canal whereby the said pharmaceutically or cosmetically active product diffuses into the follicular canal and surrounding tissue and the solid substrate forming said microspheres is rejected thereby avoiding any undesirable reaction between the organism and said solid substrate, at least 80 weight percent of said microspheres having a diameter ranging from 3 μm to 10 μm.

2. The composition of claim 1 wherein said polymer is selected from the group consisting of styrene-based polymer, a β-alanine-based polymer, a polymer derived from acrylic or methacrylic acid, a polyester derived from lactic or glycolic acid or a mixture thereof, a crosslinked protein and a protein coagulated by heat.

3. The composition of claim 1 wherein said polymer is a β-alanine based polymer.

4. The composition of claim 1 wherein said polymer is a polyester derived from lactic acid or glycolic acid or a mixture thereof.

5. The composition of claim 1 wherein said fatty substance is selected from the group consisting of a fatty alcohol and a derivative of an alcohol and a fatty acid.

6. The composition of claim 5 wherein said fatty substance has a melting point between approximately higher than 50° C. and 100° C.

7. The composition of claim 1 wherein said active product is selected from the group consisting of an agent for treating acne, a skin-reinforcing agent, a hair treating agent, an antifungal, an astringent, an antibiotic, an antiviral agent, an antihypertensive agent, an antioginal vasodilator, an agent for treating a cardiovascular disorder, an antiinflammatory agent, an antiallergen, an antiprurior, a growth factor of peptidic or proteinic nature, a neurostimulant, an antidepressant agent, a natural compound employed in neurobiological research, an anaesthetic and a hormone steroid.

8. The composition of claim 1 wherein said active product is minoxidil as an anti hair loss or regrowth agent in combination with S-carboxymethylcysteine or octopirox as an antiseborrheic agent.

9. The composition of claim 1 wherein said pharmaceutically or cosmetically acceptable carrier is an aqueous carrier or an oil.

10. The composition of claim 9 wherein said aqueous carrier is a lipophilic aqueous carrier.

11. The composition of claim 1 wherein said pharmaceutically or cosmetically acceptable carrier is a hydroalcoholic solution.

12. The composition of claim 1 wherein said pharmaceutically or cosmetically acceptable carrier is an aqueous solution of a silicone.

13. The composition of claim 1 wherein said pharmaceutically or cosmetically acceptable carrier is an aqueous carrier containing a gelling agent.

14. The composition of claim 1 wherein said microspheres are present in an amount ranging from 1 to 40 percent by weight based on the total weight of said composition.

15. The composition of claim 1 wherein said pharmaceutically or cosmetically active product is present in an amount ranging from 0.05 to 60 percent by weight based on the total weight of said composition.

16. Composition according to claim 7, characterized in that it contains vitamin A, retinoic acid or one of its derivatives, or benzoyl peroxide, as agent for treating acne.

17. Composition according to claim 7, characterized in that it contains nystatin or econazole as antifungal.

18. Composition according to claim 7, characterized in that it contains aluminium chloride as astringent.

19. Composition according to claim 7, characterized in that it contains erythromycin or tetracycline as antibiotic.

20. Composition according to claim 7, characterized in that it contains vidarabine as antiviral agent.

21. Composition according to claim 7, characterized in that it contains clonidine hydrochloride as antihypertensive.

22. Composition according to claim 7, characterized in that it contains bradikynine as vasodilator.

23. Composition according to claim 7, characterized in that it contains a peptide of the tachykinins group, in particular "substance P", as agent for treating cardiovascular disorders.

24. Composition according to claim 7, characterized in that it contains aspirin or hydrocortisone or its derivatives as antiinflammatory agent.

25. Composition according to claim 7, characterized in that it contains a chromoglycate as antiallergen.

26. Composition according to claim 7, characterized in that it contains a phenothiazine derivative as antipruritic.

27. Composition according to claim 7, characterized in that it contains the epidermic growth factor (EGF) as growth factor of peptidic nature.

28. Composition according to claim 7, characterized in that it contains caffeine or theophylline as neurostimulant.

29. Composition according to claim 7, characterized in that it contains a lithium salt as antidepressant.

30. Composition according to claim 7, characterized in that it contains capsaicine as natural compound employed in neurobiological research.

31. Composition according to claim 7, characterized in that it contains lidocaine or procaine as anaesthetic.

32. Composition according to claim 7, characterized in that it contains nitroglycerine as antianginal agent.

33. Composition according to claim 1, characterized in that the carrier is an oil consisting of a triglyceride of $C_8$–$C_{10}$ fatty acids or a mixture of several of these triglycerides, of vaseline, of liquid paraffin or of lanolin.

* * * * *